(12) United States Patent
Müller et al.

(10) Patent No.: US 9,470,420 B2
(45) Date of Patent: Oct. 18, 2016

(54) COUNTER-FLOW COMBUSTOR

(75) Inventors: Jörg Müller, Buchholz (DE); Winfred Kuipers, Essen (DE)

(73) Assignee: Bayer Intellectual Property GmbH, Monheim (DE)

( * ) Notice: Subject to any disclaimer, the term of this patent is extended or adjusted under 35 U.S.C. 154(b) by 788 days.

(21) Appl. No.: 13/387,939

(22) PCT Filed: Jul. 21, 2010

(86) PCT No.: PCT/EP2010/004441
§ 371 (c)(1),
(2), (4) Date: Feb. 21, 2012

(87) PCT Pub. No.: WO2011/015285
PCT Pub. Date: Feb. 10, 2011

(65) Prior Publication Data
US 2012/0141946 A1 Jun. 7, 2012

(30) Foreign Application Priority Data
Aug. 3, 2009 (DE) .................... 10 2009 035 762

(51) Int. Cl.
*F23R 3/28* (2006.01)
*F23C 99/00* (2006.01)
(Continued)

(52) U.S. Cl.
CPC ............... *F23R 3/28* (2013.01); *F23C 99/00* (2013.01); *F23D 14/24* (2013.01); *F23M 5/00* (2013.01); *F23C 2900/03001* (2013.01);
(Continued)

(58) Field of Classification Search
CPC ............ F23L 7/005; F23C 2900/9901; F23C 2900/03001; G01N 21/722; F23N 41/16; F23D 21/00

USPC ........................................... 431/170, 181, 11
See application file for complete search history.

(56) References Cited

U.S. PATENT DOCUMENTS 5,345,213 A * 9/1994 Semancik et al. .............. 338/34
6,193,501 B1 * 2/2001 Masel et al. .................. 431/170
(Continued)

FOREIGN PATENT DOCUMENTS

EP      2 037 264 A1    3/2009
WO    03/002247 A1    1/2003
(Continued)

OTHER PUBLICATIONS

Zimmermann et al. Miniaturized Flame Ionization Detector for Gas Chromatogrphy, Dec. 31, 2002, Sensors and Actuators B 83, pp. 285-289.*

(Continued)

*Primary Examiner* — Steven B. McAllister
*Assistant Examiner* — Rabeeul Zuberi
(74) *Attorney, Agent, or Firm* — Norris McLaughlin & Marcus PA

(57) ABSTRACT

Counterflow burner having a combustion chamber (5) to which combustible gas (B) and an oxidising agent (0) can be fed from opposite sides, having three planar substrates (1, 2, 3) which are interconnected, lying one above the other, the middle substrate (2) having the combustion chamber (5), from which passages (4), lying in the plane of the substrate, lead to the edge, the upper substrate (3) and the lower substrate (1) being closed, and at least the middle substrate (2) is produced using methods of microsystem technology.

8 Claims, 4 Drawing Sheets

(51) Int. Cl.
*F23D 14/24* (2006.01)
*F23M 5/00* (2006.01)
*G01N 21/72* (2006.01)

(52) U.S. Cl.
CPC .. *F23C 2900/9901* (2013.01); *F23N 2041/16* (2013.01); *G01N 21/72* (2013.01)

(56) References Cited

U.S. PATENT DOCUMENTS

| | | | |
|---|---|---|---|
| 6,613,972 B2 * | 9/2003 | Cohen et al. | 136/209 |
| 6,840,762 B2 | 1/2005 | Maruta | |
| 7,077,643 B2 * | 7/2006 | Holladay et al. | 431/215 |
| 7,316,563 B2 * | 1/2008 | Marshall | 431/243 |
| 2005/0287033 A1 | 12/2005 | Thurbide | |
| 2008/0213908 A1 | 9/2008 | Thurbide | |
| 2008/0295403 A1 | 12/2008 | Woods | |
| 2010/0301870 A1 | 12/2010 | Mueller et al. | |

FOREIGN PATENT DOCUMENTS

| | | |
|---|---|---|
| WO | 2006/031277 A2 | 3/2006 |
| WO | 2007/135455 A1 | 11/2007 |
| WO | 2009/036854 A1 | 3/2009 |
| WO | WO 2009036854 A1 * | 3/2009 |

OTHER PUBLICATIONS

Zimmermann. "Miniaturized flame ionization detector for gas chromatography". Mar. 15, 2002, Elsevier.*
German Search Report dated Feb. 3, 2010.

* cited by examiner

COUNTER-FLOW COMBUSTOR

This is a 371 of PCT/EP2010/004441, filed 21 Jul. 2010 (international filing date), which claims foreign priority benefit under 35 U.S.C. §119 of German Patent Application No. 10 2009 035 762.9 filed Aug. 3, 2009

The invention refers to a counterflow burner having a combustion chamber to which the combustible gas and the oxidising agent can be fed from opposite sides.

BACKGROUND OF THE INVENTION

If combustible gas and oxidising agent (e.g. hydrogen and oxygen) meet from opposite directions, their impulses are at least partially cancelled out. Thus, a flame front, which can be not only of an elongated shape but also of a spherical shape, is achieved. This is not the case with a premix flame since both gases flow basically in one direction there. Also, a diffusion flame is less advantageous since diffusion has to take place there. The flame is also at a distance from the nozzles so that only a small amount of heat is dissipated via the nozzles. Lower gas velocities, especially lower exhaust gas velocities, are also possible, as a result of which heat losses are reduced as a result of forced convection.

All this contributes towards increasing the flame temperature in the process. Finally, a longer residence time of the sample gas to be analysed in the combustion chamber is also achieved. The spherical shape is especially favourable for the flame stability on account of the minimum surface over which the heat is dissipated in comparison to the volume in which the heat is generated.

This is extremely important if the aim is to use only very small flames, as is necessary in miniaturised scientific instruments or gas detectors, for example. Miniaturized counterflow burners, in which the combustion chamber is encompassed by a capillary consisting of stainless steel, are known for such analyses (US2005/0287033A1, US2008/0213908A1). The production of corresponding small capillaries is certainly possible. The assembly of corresponding counterflow burners, which consist of different parts, gives rise to considerable difficulties and costs, however, especially when the desire would be to use structures which are as small as possible and when these are to be produced in batch production. Furthermore, a capillary extends only in one direction, that is to say it is an essentially one-dimensional structure, so that only comparatively few ways exist of influencing the flame.

These micro-counterflow burners are used for example for photometric gas chromatography and gas chromatography with measurement of the generated ionisation. Corresponding devices can serve in this case not only for scientific purposes but are also suitable, for example, for being used in environmental technology in order to determine harmful gases.

The object of the invention exists in the creation of a counterflow burner of small dimensions which is to be inexpensively produced.

SUMMARY OF THE INVENTION

The solution according to the invention is that the counterflow burner has three planar substrates which are interconnected, lying one above the other, that the middle substrate has the combustion chamber, from which passages, lying in the plane of the substrate, lead in opposite directions to the edge, that the upper substrate and the lower substrate are basically closed, and that at least the middle substrate is produced using methods of microsystem technology.

The counterflow burner therefore no longer consists basically of capillaries but of planar structures. These can be processed particularly well, especially also with methods of microsystem technology, so that very small counterflow burners can be achieved. The combustion chamber, from which passages, lying in the plane of the substrate, lead in opposite directions to the edge, is arranged in the middle substrate. This middle substrate with the combustion chamber and the passages is then covered by means of basically closed upper and lower substrates.

DETAILED DESCRIPTION

The initially open passages and the open combustion chamber, which are produced by means of the known methods of microsystem technology, are at least basically closed off by means of these upper and lower substrates. Since the passages lead in opposite directions from the combustion chamber to the edge, the gases, which are introduced through these passages from opposite directions, collide, as a result of which the impulse is at least partially compensated.

In a preferred embodiment, provision is made for two such passages which are directed towards each other, wherein the combustible gas is fed to the combustion chamber through one passage and the oxidising agent is fed through the other.

In a further preferred embodiment, the upper and the lower substrates completely close off the middle substrate. The feed of combustible gas and oxidising agent and also the discharge of the exhaust gases therefore takes place in the plane of the middle substrate at its edge. As a result of the arrangement of the passages, it is ensured in this case that the gases meet in a suitable manner in each case. The exhaust gases can then be discharged through corresponding passages which also extend from the combustion chamber in opposite directions.

A preferred embodiment is distinguished by the fact that the passages which lie in the plane of the substrate lead from the combustion chamber to the edge in a star-like manner. As a result, access to the combustion chamber is provided not only from two sides but from a plurality of sides, which can serve for controlling or homogenising the flame.

In contrast to cases where combustible gas and oxidising agent meet from opposite directions, the net impulse of the meeting gases can then even be made to amount to zero.

If oxygen and double the amount of hydrogen meet in order to burn as oxyhydrogen gas, then the oxygen, on account of the greater molecular weight, has a greater impulse than the hydrogen so that the impulses do not completely add up to zero. With the star-like arrangement of the invention, however, the gases can be allowed to meet from a plurality of sides and in this case two oxygen streams and two combustible gas streams can be allowed to always meet from exactly opposite directions so that the overall impulse adds up to zero.

In this way, a particularly good spherical shape is achieved and, as a result, a particularly high temperature of the flame. Compensation of the impulses can also be consequently achieved if the sample to be analysed is air which in fact consists of 80% nitrogen. If the air to be analysed is added to the hydrogen-combustible gas, this gas has approximately the same molecular weight as the oxygen which is fed from the opposite direction. With the star-like arrangement, an oxygen surplus is also possible in the process, which provides a higher ion yield.

In a preferred embodiment, the upper and the lower substrates completely close off the middle substrate so that all the gases in the plane of the middle substrate enter the combustion chamber and leave this. In a further preferred embodiment, the upper substrate and the lower substrate have openings which lead to the combustion chamber and through which gas can enter or discharge in a direction perpendicular to the plane of the substrate. Naturally, here two openings in each case must be oppositely disposed so that the gas can enter or discharge through the two openings in opposite directions.

All these embodiments have the advantage that they operate regardless of position. They therefore do not have to be precisely orientated for operation and can even be inverted.

The middle substrate advantageously consists of silicon which can be processed particularly well with the aid of microsystem technology.

In a further preferred embodiment, the upper substrate and/or the lower substrate consist(s) of borosilicate glass. On the one hand, this borosilicate glass can also be structured with the aid of microsystem technology. It can also be bonded to silicon using the anodic bonding process so that the production of the counterflow burner of the invention presents no problems. Finally, it also has a low thermal conductivity, as a result of which heat losses are reduced, which increases flame stability and flame temperature. The passages can be formed as desired in the middle substrate with the aid of microsystem technology. They can also be formed in this case so that heat exchangers are formed by the exhaust gas passages being provided at least on the edge of the middle substrate very close to the passages for the combustion gas or oxidising agent and running to the combustion chamber in a star-like manner only in the middle section.

The passages for at least one of the gas flows are expediently connected to a pressure compensating chamber which surrounds the counterflow burner, in order to be sure that the combustible gas and/or the oxidising agent actually enter(s), or the exhaust gases discharge, through all the passages with the same velocity.

In an advantageous embodiment, the flame stabilising elements in the combustion chamber are attached on the upper substrate and/or on the lower substrate. These can be cylindrical elements, for example, which cylindrically encompass the actual flame.

In the star-like arrangement, the passages are expediently directed towards the middle point of the combustion chamber so that the impulses of the incoming gas streams add up to zero. It is also possible, however, to direct the passages tangentially towards the circumference of an imaginary cylinder which is arranged coaxially in the combustion chamber. In this way, a vortical flame is achieved.

The upper substrate and/or the lower substrate can be coated in the region of the combustion chamber with materials which accelerate the combustion, e.g. with platinum, which is applied using methods of microsystem technology such as cathode sputtering or vapour deposition.

As was mentioned above, when equal amounts of hydrogen and oxygen meet, no resulting overall zero impulse occurs. This is applicable at least at the same flow velocities. A measure in addition to the aforesaid measures to avoid or at least to reduce this problem is to allow the oxygen to enter the combustion chamber at a lower velocity than the hydrogen. This can be achieved in particular by the passages having different cross sections in the end region which is directed towards the combustion chamber, specifically a larger cross section in the passages which are provided for the oxygen.

As mentioned, the upper substrate and the lower substrate can also be structured using methods of microsystem technology in order to allow the combustion chamber to reach into these substrates, for example, or in order to increase the cross sections of the passages.

Microsystem technology additionally offers the advantage that even more characteristics and shapes, which are important for special application purposes, can be achieved.

As was mentioned in the introduction, one of the many applications of a counterflow burner with low gas consumption is the flame ionisation detector. It is indeed known to produce a flame ionisation detector with the aid of microsystem technology (WO 2009/036854 A1). With this detector, however, combustible gas and oxidising agent are not fed separately, and more especially not from opposite sides, but enter the combustion chamber already as an oxyhydrogen gas mixture. The particular advantages of the spherical flame cannot be achieved in this way.

Normally, a flame ionisation detector is operated with high hydrogen flow at ten times the amount of support air, which is necessary on account of the oxygen requirement and the screening. In a planar microburner, the flame is screened by the burner itself so that support air can be dispensed with and the flame can be operated with oxyhydrogen gas (WO 2009/036854 A1). Using the counterflow method, according to the invention, of the microburner, the consumption of hydrogen and oxygen can be reduced still further without the flame losing its ionising power.

For the function of the flame ionisation detector, the planar microburner has to be equipped with three electrodes, these being an anode and a cathode, via which the voltage is applied, and a protective electrode which prevents leakage flows, which flow through the glass, being detected in addition.

The counterflow burner can also be used for flame spectrometry. Depending upon the method of analysis, either only an optical spectrometer (atomic emission spectrometer, chemical luminescence spectrometer) or also a radiation source is additionally used (atomic absorption spectrometry, atomic fluorescence spectrometry).

For gas analysis, screening of the flame from the environment is of significance in order to avoid spurious signals. To this end, the openings of the gas discharge must be of a sufficiently small design. In order to prevent a pressure increase, which impairs the flame stability, in the combustion chamber, the gas can be pumped out. At the same time, the negative pressure which is created in the chamber can be used for the sampling.

The invention is described by way of example in the following text based on advantageous embodiments with reference to the attached drawings.

Figure 1:
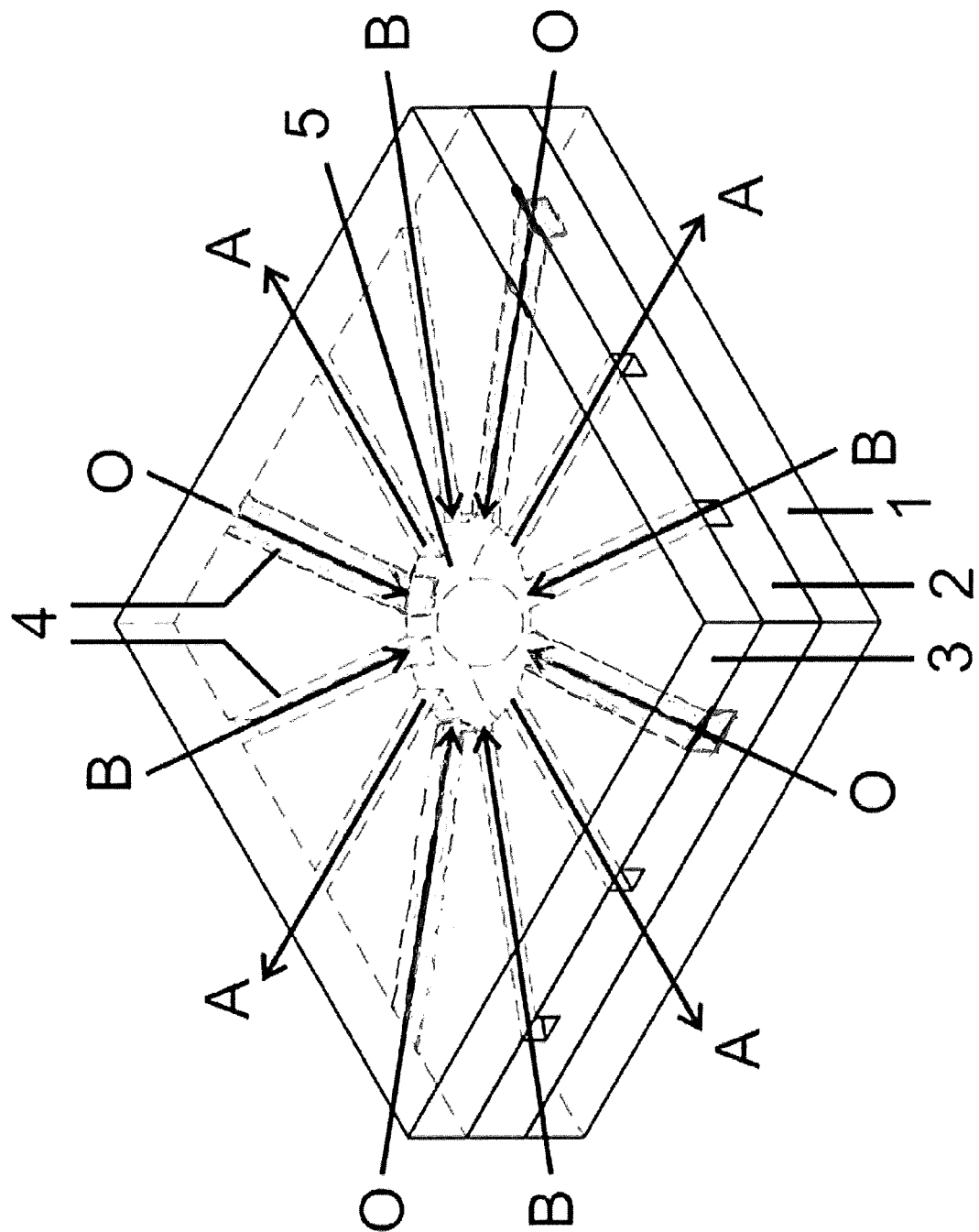
FIGS. 1-5 show five different embodiments in a schematic view.

As is shown in FIGS. 1-5, the counterflow burner of the invention has three substrates, in the present case being a lower substrate 1 consisting of borosilicate glass, a middle substrate 2 consisting of silicon, and an upper substrate 3 consisting of borosilicate glass. Passages 4 are arranged in the middle substrate 2 and are directed towards the combustion chamber 5 in a star-like manner. The gases flow in each case in the direction of the arrows into the combustion chamber 5 or flow out of it. In this case, the flow directions of the combustible gases are designated "B", the flow directions of the oxidising agent are designated "0", and the flow directions of the exhaust gases are designated "A". In the embodiment of FIG. 1, two combustible gas streams meet in each case, two oxidising agent streams meet in each case, and two oppositely directed exhaust gas streams A leave the combustion chamber 5 in each case. In this way, the impulse of the flame is altogether zero.

Figure 2:
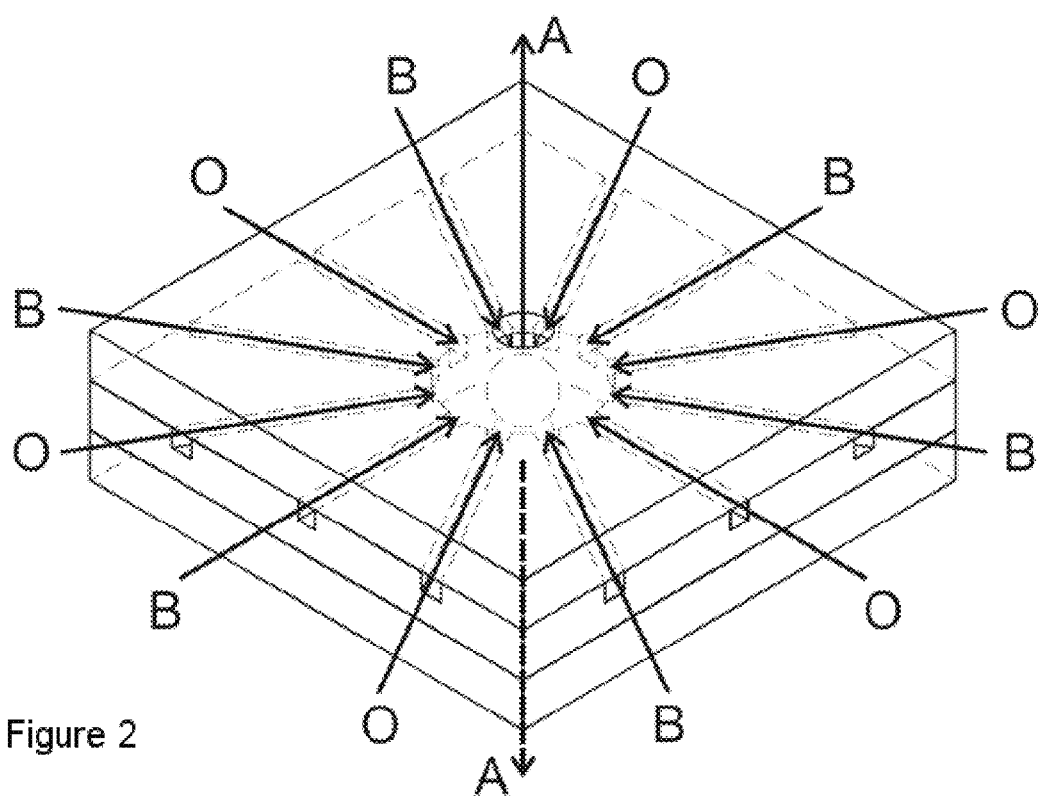

Also, in the embodiment of FIG. 2, combustible gases B and oxidising agent 0, by means of the passages, in each case meet in an opposed manner in the combustion chamber 5. The exhaust gases, however, leave the combustion chamber in the direction perpendicular to the plane of the substrates through corresponding openings, which is indicated by the dashed arrows A.

Figure 3:
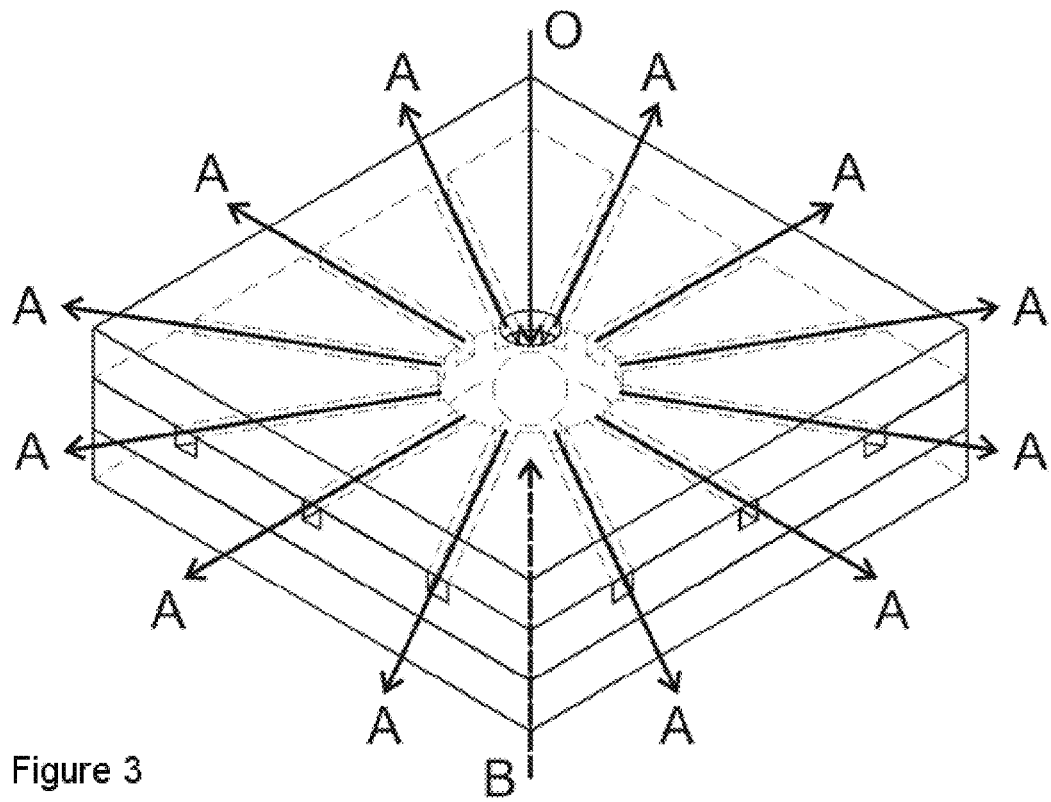

In the embodiment of FIG. 3, combustible gas B and oxidising agent 0 enter the combustion chamber from the top or bottom in a direction perpendicular to the plane of the substrates, whereas the exhaust gas A leaves the combustion chamber through the passages in the middle substrate 2.

Figure 4:
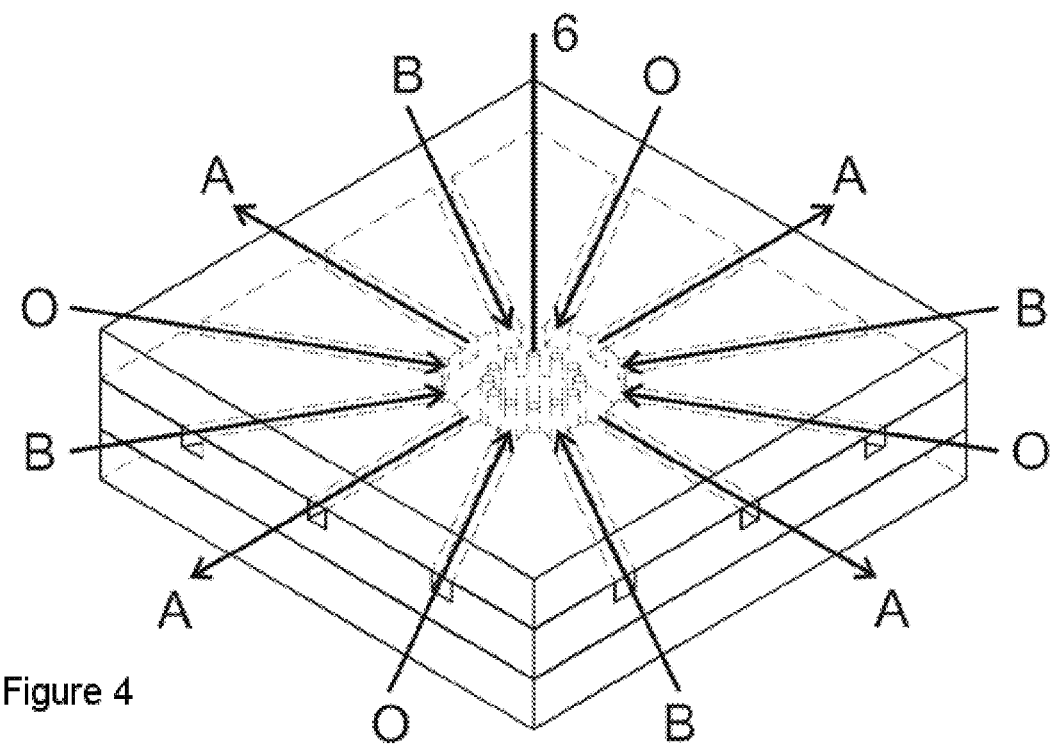

In the embodiment of FIG. 4, as in the embodiments of FIGS. 1 and 2, two combustible gas streams again meet, two oxidising agent streams again meet, and two exhaust gas streams A leave the combustion chamber 5 again in opposite directions. However, small cylinders are provided—arranged on the lower substrate 1 or on the upper substrate 3—which encompass the actual space in which the combustion takes place. These upright cylinders are arranged on a cylindrical generated surface around the centre of the combustion chamber.

Figure 5:
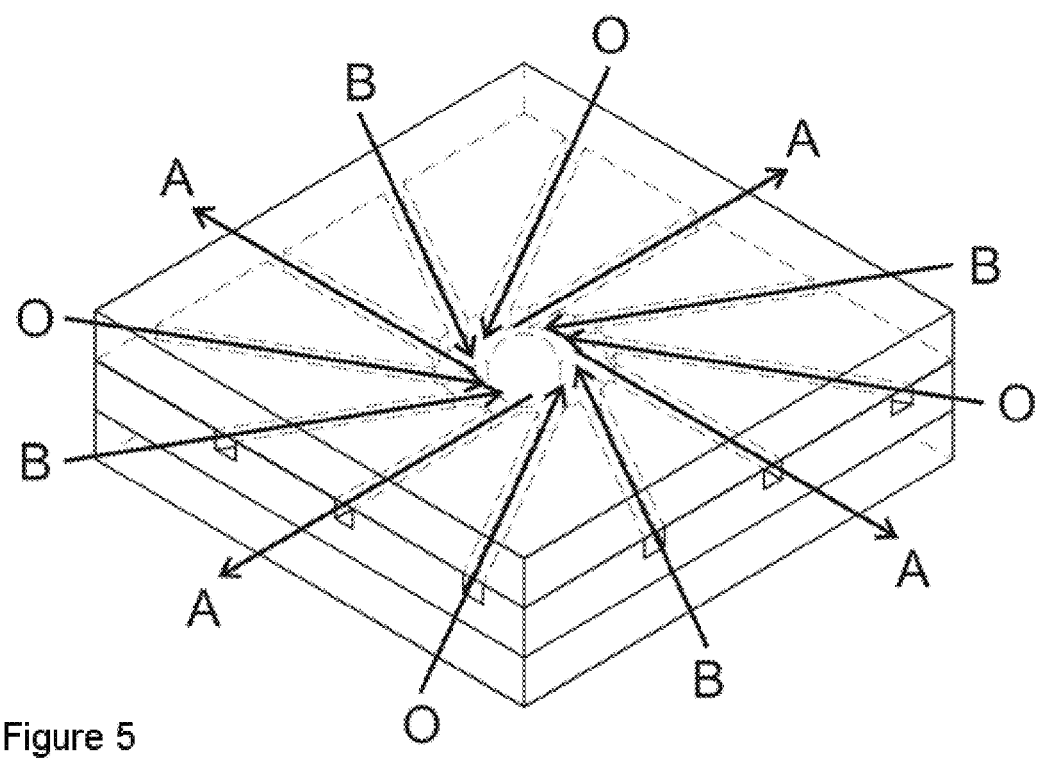

In the embodiment of FIG. 5, the gases are not directed towards the centre of the combustion chamber 5 or directed away from it, but enter the combustion chamber tangentially, as a result of which a stable flame vortex is created. As was mentioned further up, the star-like arrangement has certain advantages. In many other cases, however, this star-like arrangement is dispensed with and, for example, use is made of only two passages which are directed towards each other from opposite directions and through which is fed combustible gas on one side and oxidising agent on the other side.

The invention claimed is:

1. Counterflow burner comprising: a combustion chamber (5) and passages (4) for conveying a combustible gas (B) and an oxidizing agent gas (0) to the combustion chamber from different directions, having three planar substrates (1, 2, 3) which are interconnected, lying one above the other, the middle substrate (2) having the combustion chamber (5), from which the passages (4), lying in the plane of the middle substrate, lead in opposite directions to the edge of the substrate in a radial manner, and the combustible gas (B) and the oxidizing agent (0) introduced through the passages from opposite directions collide in the combustion chamber so two oxidizing agent gas streams and two combustible gas streams meet from exactly opposite directions and achieve a flame front having a spherical shape, and at least the middle substrate (2) being configured as a microsystem;

wherein the upper substrate (3) and the lower substrate (1) are closed except for openings which are directed towards the combustion chamber and through which gas can enter or discharge perpendicularly to the plane of the substrates.

2. Counterflow burner according claim 1, wherein the upper substrate (3) and/or the lower substrate (1) are, or is, also structured using methods of microsystem technology.

3. Counterflow burner according to claim 1, wherein the middle substrate (2) consists of silicon.

4. Counterflow burner according to claim 1, wherein the upper substrate (3) and/or the lower substrate (1) consist(s) of borosilicate glass.

5. Counterflow burner according to claim 1, wherein flame stabilising elements (6) are applied to the upper substrate (3) and/or to the lower substrate (1).

6. Counterflow burner according to claim 1, wherein the passages (4) are directed towards the middle point of the combustion chamber (5).

7. Counterflow burner according to claim 1, wherein the passages (4) have different cross sections in the end region which is directed towards the combustion chamber (5).

8. Counterflow burner according to claim 1, wherein the upper substrate (3) and/or the lower substrate (1) are, or is, coated in the region of the combustion chamber (5) with materials which accelerate combustion.

* * * * *